(12) United States Patent
Takatsuji et al.

(10) Patent No.: US 7,282,622 B2
(45) Date of Patent: Oct. 16, 2007

(54) FLOWER MORPHOLOGY OF PLANTS BY TARGETING MADS-BOX GENE

(75) Inventors: Hiroshi Takatsuji, Tsukuba (JP); Meenu Kapoor, Tsukuba (JP)

(73) Assignees: National Institute of Agrobiological Sciences, Ibaraki (JP); National Agriculture and Bio-Oriented Research Organization, Saitama (JP)

( * ) Notice: Subject to any disclaimer, the term of this patent is extended or adjusted under 35 U.S.C. 154(b) by 194 days.

(21) Appl. No.: 10/169,426

(22) PCT Filed: Oct. 30, 2001

(86) PCT No.: PCT/JP01/09511

§ 371 (c)(1),
(2), (4) Date: Jan. 31, 2003

(87) PCT Pub. No.: WO02/36776

PCT Pub. Date: May 10, 2002

(65) Prior Publication Data

US 2004/0255349 A1    Dec. 16, 2004

(30) Foreign Application Priority Data

Oct. 30, 2000   (JP)   ............................ 2000-330642

(51) Int. Cl.
*C12N 15/29*   (2006.01)
*C12N 15/82*   (2006.01)
*C12N 5/04*    (2006.01)
*A01H 5/00*    (2006.01)

(52) U.S. Cl. ...................... 800/278; 800/298; 800/290; 536/23.6; 435/320.1; 435/419; 435/468

(58) Field of Classification Search ................ 800/286, 800/290, 298, 278; 536/23.6; 435/320.1, 435/419, 468
See application file for complete search history.

(56) References Cited

U.S. PATENT DOCUMENTS 5,744,693 A   4/1998   Meyerowitz et al. ....... 800/205

FOREIGN PATENT DOCUMENTS

WO   WO99/04003   1/1999
WO   WO 00/32780  6/2000

OTHER PUBLICATIONS

Suguru Tsuchimoto et al., Ectopic Expression of pMADS3 in Transgenic Petunia Phenocopies The Petunia Blind Mutant. The Plant Cell Aug. 1993, vol. 5, No. 8, pp. 843-853.*
Branch, A., A Good Antisense Molecule is Hard to Find. TIBS, 23:45-50, 1998.*
Mizukami et al., Functional Domains of The Floral Regulator AGAMOUS: Characterization of The DNA Binding Domain and Analysis of Dominant Negative Mutations, The Plant Cell, 8:831-845, 1996.*
Kapoor et al. *Plant J.*, 32(1):115-127 (2002).
European Search Report for EP 01 97 6874, mailing date: Dec. 27, 2004.
Hareven, et al. (1994). *Euphytica* 79:235-243.
Honma and Goto (2001). *Nature* 409(6819):525-529.
Tsuchimoto, et al. (1993). *The Plant Cell* 5(8):843-853.
Van der Krol, et al. (1988). *Nature* 333:866-869.
Yanofsky et al. *Nature*, 346(6279):35-9 (1990).
Scutt et al. *Dev. Genet.*, 25(3):267-79 (1999).
Bowman et al. *Development*, 112:1-20 (1991).
Ecker et al. *Proc. Natl. Acad. Sci. USA*, 83:5372-5376 (1986).
Horsch et al. *Science*, 227:1229-1231 (1985).
Kempin et al. *Plant Physiol.*, 103: 1041-1046 (1993).
Martienssen, R., *Curr. Biol.*, 6(7):810-813 (1996).
Yuyama et al . *Biochem. Biophys. Res. Commun.*, 186(3):1271-1279 (1992).

* cited by examiner

*Primary Examiner*—Stuart F. Baum
(74) *Attorney, Agent, or Firm*—Ingrid A. Beattie; Cynthia A. Kozakiewicz; Mintz Levin

(57) ABSTRACT

Genomic DNA containing the promoter region of the pMADS3 gene was isolated, ligated to a reporter gene, and then introduced into petunia plants via an *Agrobacterium*-mediated method. Surprisingly, the resultant plants became double-flowered by conversion of stamens into petaloid structures.

10 Claims, 3 Drawing Sheets

US 7,282,622 B2

FLOWER MORPHOLOGY OF PLANTS BY TARGETING MADS-BOX GENE

TECHNICAL FIELD

The present invention relates to alteration of flower morphology of plants employing genetic engineering technology.

BACKGROUND ART

The trait of double-flowered or multi-flowered petals is one of the important factors for ornamentalness of garden plants. Introduction of morphological traits into flowers of garden plants, such as producing multi-flowers via genetic engineering techniques may produce a great diversity of varieties in shorter periods of time than the conventional crossbreeding techniques.

MADS-box genes are a family of genes consisting of 30 or more genes that encode transcription factors having a conserved region called MADS-box. Many of these genes have been shown to regulate morphogenesis and organogenesis of plants by way of transcriptional regulation. Many of the genes of the three classes of homeotic genes that are responsible for development of floral organs (the ABC model) are MADS-box genes and have been studied in detail (Sakai, H. (2000). "Molecular genetics of floral morphogenesis," in: "Molecular Mechanisms for Determination of Plant Morphology," 150–163 (Shujunsha Inc.); Goto, K. (1994). "The ABCs of Flower Development: Genetic and Molecular Analyses of Floral Homeotic Genes," in: Molecular Mechanisms for Determination of Plant Morphology, 52–61 (Shujunsha. Inc.); and Weigel, D., and Meyerowitz, E. M. (1994). Cell 78, 203–209).

One of the MADS-box transcription factors isolated from *Petunia*, pMADS3 (MADS3 derived from *Petunia*), is a homeotic gene involved in specificity of floral organs. Its structure and expression pattern suggest that pMADS3 belongs to Class C of the floral ABC model. It was revealed that homeotic mutations, such as formation of antheroid structure (staminody) at the tip of petals and, occasionally, carpelloid structure at the tip of sepals, occur in transgenic petunia plants that ectopically express the pMADS3 gene. Such mutations also suggest that MADS3 is a member of the Class C genes (Tsuchimoto, S. et al. (1993) Plant Cell 5, 843–853; Takatsuji, H. (1994). "Transcription Factors Controlling Floral Organ Development," in: Molecular Mechanisms for Determination of Plant Morphology, 96–106 (Shujunsha Inc.)). The cDNA sequence of pMADS3 has been reported in Tsuchimoto, S. et al. (1993). Plant Cell 5, 843–853.

As described above, many reports on MADS-box transcription factors and their functions in floral organogenesis in plants are available. However, so far no one has reported success in producing highly ornamental plants, such as multi-flowered plants, using a MADS-box transcription factor as the target.

DISCLOSURE OF THE INVENTION

An object of this invention is to alter flower morphology of plants by targeting a MADS-box transcription factor, so as to produce ornamental plants of novel aesthetic value.

The pMADS3 gene is specifically expressed in stamens and carpels (Tsuchimoto, S. et al. (1993). Plant Cell 5, 843–853; Takatsuji, H. (1994). "Transcription Factors Controlling Floral Organ Development," in: Molecular Mechanisms for Determination of Plant Morphology, 96–106 (Shujunsha Inc.)). Based on this finding, the present inventors first isolated genomic DNA containing the promoter region of pMADS3 that shows the above tissue specificity, and isolated the DNA of interest from a petunia genomic library. To detect the tissue-specific promoter activity of the isolated genomic DNA, it was ligated to the reporter GUS gene and then introduced into petunia plants via an *Agrobacterium*-mediated method.

Surprisingly, this transformation led to silencing of the pMADS3 gene in the petunia plants and conversion of stamens into petaloid structures, thereby producing double-flowers. Five of 12 transgenic strains showed the double-flower trait. Also, these plants gave rise to immature secondary flowers and sepaloid-petaloid organs in the internal region of the stamens that turned into petals as well as produced double-flowers. Hence, the inventors unexpectedly found that silencing the pMADS3 gene in petunia plants by introduction of isolated DNA therein was successful in creating petunia plants having multi-flowers, a useful morphological trait for ornamental plants. These results suggest that suppression of the MADS3 function in plants may contribute to improvement of their flower morphology.

The present invention relates to alteration of flower morphology by suppression of the function of the MADS3 gene. Specifically, the present invention is directed to the following:

(1) A DNA molecule for alteration of flower morphology of plants, selected from the group consisting of:
   (a) a DNA molecule encoding antisense RNA complementary to the transcript of the MADS3 gene;
   (b) a DNA molecule encoding RNA having ribozyme activity that specifically cleaves the transcript of the MADS3 gene;
   (c) a DNA molecule encoding RNA that suppresses the expression of the MADS3 gene by cosuppression in the plant cells, wherein said DNA molecule has at least 90% homology to the MADS3 gene; and
   (d) a DNA molecule encoding a protein having a dominant negative phenotype for the endogenous MADS3 protein in the plant cells.

(2) The DNA molecule according to (1), wherein the alteration of flower morphology of plants is at least one selected from the group consisting of conversion of stamens into petals, formation of secondary flowers and formation of sepaloid-petaloid structures.

(3) A vector comprising the DNA molecule according to (1) or (2).

(4) A transformed plant cell retaining the DNA molecule according to (1) or (2), or the vector according to (3).

(5) A transgenic plant comprising the transformed plant cell according to (4).

(6) A progeny or clone of the transgenic plant according to (5).

(7) The plant according to (5) or (6), wherein said plant has an alteration in the flower morphology compared to the wild-type plant.

(8) The plant according to (7), wherein said alteration in the flower morphology is at least one selected from the group consisting of conversion of stamens into petals, formation of secondary flowers and formation of sepaloid-petaloid structures.

(9) A reproductive material of the plant according to any one of (5) to (8).

(10) A method for producing a plant having an alteration in the flower morphology, comprising the steps of:

(a) introducing the DNA molecule according to (1) or a vector carrying said DNA molecule into a plant cell; and (b) regenerating a plant from said plant cell.

(11) The method according to (10), wherein said alteration of flower morphology of plants is at least one selected from the group consisting of conversion of stamens into petals, formation of secondary flowers and formation of sepaloid-petaloid structures.

As used herein, the term "MADS3 gene" refers to the MADS3 gene of *Petunia* (the pMADS3 gene) and a gene homologous thereto present in other plants.

As used herein, the term "stamens" refers to one of the floral organs of seed plants, a male reproductive organ, which has a structure comprising a filament with an anther at its top.

As used herein, the term "petals" refers to a sterile floral leaf that constitutes a corolla.

As used herein, the term "secondary flowers" refers to a structure that occurs in the internal part of a flower and is similar to an authentic (external) flower.

As used herein, the term "sepaloid-petaloid structure" refers to a mosaic structure comprising a portion showing the sepaloid feature and a portion showing the petaloid feature in a floral organ.

In the present invention, target MADS3 genes for alteration of flower morphology are not limited to any particular genes as long as the genes can regulate the floral organogenesis in the plant that retains the genes. Preferably, they are the MADS3 genes derived from ornamental plants such as *Petunia,* Torenia and Lisianthus. As used herein, the phrase "alteration in flower morphology" refers to that flower morphology of a plant of interest differs from that of the unaltered plant. The alterations of flower morphology in the present invention include conversion of stamens into petals, formation of secondary flowers and formation of sepaloid-petaloid structures. Among these, conversion of stamens into petals is preferable from the standpoint of increasing the aesthetic value of the flowers.

According to the present invention, an alteration of flower morphology of plants is achieved by suppressing the MADS3 function. As used herein, the phrase "suppressing the MADS3 function" refers to an interference with the process from transcription of the MADS3 gene to functional expression of the MADS3 protein, including suppression of the expression (transcription and translation) of the MADS3 gene and of suppression of the function of the MADS3 protein. "Suppression" used herein includes partial suppression as well as complete suppression.

The alteration of flower morphology in a plant can be achieved by suppressing expression of the endogenous MADS3 gene in the plant. The expression of a specific endogenous gene in plants can be suppressed by conventional methods utilizing antisense technology. Ecker et al. were the first to demonstrate the effect of an antisense RNA introduced by electroporation into plant cells by using the transient gene expression method (Ecker, J. R. and Davis, R. W. (1986). Proc. Natl. Acad. Sci. USA 83, 5372). Thereafter, target gene expression was reportedly reduced in tobacco and petunias by expressing antisense RNAs (van der Krol, A. R. et al. (1988). Nature 333, 866). The antisense technique has now been established as a means to suppress target gene expression in plants.

Multiple factors cause antisense nucleic acids to suppress target gene expression. These include inhibition of transcription initiation by triple strand formation; suppression of transcription by hybrid formation at the site where the RNA polymerase has formed a local open loop structure; transcription inhibition by hybridization with the RNA being synthesized; suppression of splicing by hybrid formation at the junction between an intron and an exon; suppression of splicing by hybrid formation at the site of spliceosome formation; suppression of mRNA translocation from the nucleus to the cytoplasm by hybridization with mRNA; suppression of splicing by hybrid formation at the capping site or at the poly A addition site; suppression of translation initiation by hybrid formation at the binding site for the translation initiation factors; suppression of translation by hybrid formation at the site for ribosome binding near the initiation codon; inhibition of peptide chain elongation by hybrid formation in the translated region or at the polysome binding sites of mRNA; and suppression of gene expression by hybrid formation at the sites of interaction between nucleic acids and proteins. These factors suppress target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319–347, (1993)).

An antisense sequence of the present invention can suppress target gene expression by any of the above-mentioned mechanisms. If an antisense sequence is designed to be complementary to the untranslated region near the 5' end of the gene's mRNA, it will effectively inhibit translation of a gene. Additionally, it is also possible to use sequences that are complementary to the coding regions or to the untranslated regions on the 3' side. Thus, the antisense DNA used in the present invention includes a DNA having antisense sequences against both the untranslated regions and the translated regions of the gene. The antisense DNA to be used is connected downstream of an appropriate promoter, and, preferably, a sequence containing the transcription termination signal is connected on the 3' side. The DNA thus prepared can be transfected into the desired plant via standard methods. The sequence of the antisense DNA is preferably a sequence complementary to the endogenous gene of the plant to be transformed or a part thereof, but it need not be perfectly complementary so long as it can effectively inhibit the gene expression. The transcribed RNA is preferably 90% or more, and most preferably 95% or more, complementary to the transcribed products of the target gene. The complementarity of sequences can be determined by the above-described search methods. In order to effectively inhibit the expression of the target gene by means of an antisense sequence, the antisense DNA should be at least 15 nucleotides long or more, preferably 100 nucleotides long or more, and most preferably 500 nucleotides long or more. The antisense DNA to be employed is generally shorter than 5 kb, preferably shorter than 2.5 kb.

SEQ ID NO: 1 shows the nucleotide sequence of the genomic DNA fragment from *Petunia* which can be used to generate a DNA construct that can suppress the pMADS3 function. The cDNA sequence of this gene is disclosed in Tsuchimoto, S. et al. (1993). Plant Cell 5, 843–853; Takatsuji, H. "Transcription Factors Controlling Floral Organ Development" in Molecular Mechanisms for Determination of Plant Morphology, 96–106 (Shujunsha Inc., 1994).

The DNA derived from any plant (other than *Petunia*) maybe isolated and sequenced utilizing a hybridization technique (Southern, E. M. (1975). Journal of Molecular Biology 98, 503) and a polymerase chain reaction (PCR) technique (Saiki, R. K. et al. (1985). Science 230, 1350–1354; Saiki, R. K. et al. (1988). Science 239, 487–491). Both of these are well known to one skilled in the art. Hybridization reactions to isolate such DNAs are preferably conducted under stringent conditions. Stringent hybridization conditions of the present invention include conditions such as: 6 M urea, 0.4% SDS, and 0.5×SSC. DNAs with greater homology may be isolated efficiently when hybridization is performed under conditions with higher stringency, such as, 6 M urea, 0.4% SDS, and 0.1×SSC. The DNA thus isolated may be sequenced by any known nucleotide sequencing method.

DNA encoding ribozymes can also be used to suppress the expression of endogenous genes. A ribozyme is defined as an RNA molecule that has catalytic activity. Numerous ribozymes are known in literature, each having distinct catalytic activity. Research on ribozymes as RNA-cleaving enzymes has enabled the designing of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka. (1990). Tanpakushitsu Kakusan Kohso (Nucleic acid, Protein, and Enzyme) 35, 2191).

The self-cleavage domain of a hammerhead type ribozyme cleaves at the 3' side of C15 sequence G13U14C15. Formation of a nucleotide pair between U14 and A at the ninth position is considered important for the ribozyme activity. It has been shown that the cleavage also occurs when the nucleotide at the 15th position is A or U instead of C (Koizumi, M. et al. (1988). FEBS Lett. 228, 225). If the substrate-binding site of the ribozyme is designed to be complementary to the RNA sequences adjacent to the target site, one can create a restriction-enzyme-like RNA cleaving ribozyme that recognizes the sequence UC, UU, or UA within the target RNA (Koizumi, M. et al. (1988). FEBS Lett. 239, 285; Makoto Koizumi and Eiko Ohtsuka .(1990). Tanpakushitsu Kakusan Kohso (Protein, Nucleic acid, and Enzyme) 35, 2191; Koizumi, M. et al. (1989). Nucleic Acids Res. 17, 7059). In the pMADS3 gene, there are pluralities of sites that can be used as the ribozyme target.

The hairpin type ribozyme is also useful in the present invention. A hairpin type ribozyme can be found, for example, in the minus strand of the satellite RNA of tobacco ringspot virus (Buzayan, J. M. (1986). Nature 323, 349). This ribozyme has also been shown to target-specifically cleave RNA (Kikuchi, Y. and Sasaki, N. (1992). Nucleic Acids Res. 19, 6751; Kikuchi, Y. (1992) Kagaku To Seibutsu (Chemistry and Biology) 30, 112).

The ribozyme designed to cleave the target is fused with a promoter, such as the cauliflower mosaic virus 35S promoter, and with a transcription termination sequence, so that it will be transcribed in plant cells. If extra sequences are added to the 5' end or the 3' end of the transcribed RNA, the ribozyme activity may be lost. In this case, one can place an additional trimming ribozyme, which functions in the cis position to perform the trimming on the 5' or the 3' side of the ribozyme portion, thereby precisely cutting the ribozyme portion from the transcribed RNA containing the ribozyme (Taira, K. et al. (1990). Protein Eng. 3, 733; Dzaianott, A. M. and Bujarski, J. J. (1989). Proc. Natl. Acad. Sci. USA86, 4823;Grosshands, C. A. and Cech, R. T. (1991). Nucleic Acids Res. 19, 3875; and Taira, K. et al. (1991). Nucleic Acid Res. 19, 5125). Multiple sites within the target gene can be cleaved by arranging these structural units in tandem to achieve greater effects (Yuyama, N. et al. (1992). Biochem. Biophys. Res. Commun. 186, 1271). By using such ribozymes, it is possible to specifically cleave the transcription products of the target gene in the present invention, thereby suppressing the expression of the gene.

Endogenous gene expression can also be suppressed by cosuppression through transformation by DNA having a sequence identical or similar to the target gene sequence. "Cosuppression," as used herein, refers to the phenomenon in which, when a gene having a sequence identical or similar to the target endogenous gene sequence is introduced into plants by transformation, expression of both the introduced exogenous gene and the target endogenous gene becomes suppressed. Although the detailed mechanism of cosuppression is unknown, it is frequently observed in plants (Curr. Biol. (1997). 7, R793; Curr. Biol. (1996). 6, 810). For example, if one wishes to obtain a plant body in which the MADS3 gene is cosuppressed, the plant in question can be transformed with a DNA vector designed so as to express the MADS3 gene or DNA having a similar sequence to select a plant having the target phenotype among the resultant plants, for example, a plant with petaloid stamens. The gene to be used for cosuppression does not need to be completely identical to the target gene, but it should have at least 70% or more sequence identity, preferably 80% or more sequence identity, and more preferably 90% or more (e.g., 95% or more) sequence identity.

The identity of one amino acid sequence or nucleotide sequence to another can be determined by following the BLAST algorithm by Karlin and Altschl (Proc. Natl. Acad. Sci. USA (1993). 90, 5873–5877). Programs such as BLASTN and BLASTX were developed based on this algorithm (Altschul et al. (1990). J. Mol. Biol. 215, 403–410). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST programs. Specific techniques for such analysis are known in the art (National Center for Biotechnology Information, National Library of Medicine, Bethesda, Md. 20894).

In addition, endogenous gene function in the present invention can also be suppressed by transforming the plant with a gene encoding a protein having the dominant negative phenotype of the expression product of the target gene. "A DNA encoding a protein having the dominant negative phenotype" as used herein means a DNA encoding a protein which, when expressed, can eliminate or reduce the activity of the protein encoded by the endogenous gene inherent to the plant. An example thereof is a DNA that codes for a peptide having DNA binding ability and having no transcription-activating domain of the protein of the present invention.

To produce a transgenic plant in which the MADS3 gene function is suppressed, the aforementioned DNA that suppresses the MADS3 function is inserted into an appropriate vector and then introduced into plant cells. Transformed plant cells are subsequently regenerated into plants. The vector used to transform plant cells is not particularly restricted as long as it is capable of expressing an inserted gene in the cells. For example, a vector having a promoter for performing constitutive gene expression in plant cells (e.g., the 35S promoter of cauliflower mosaic virus), or a vector having a promoter that is inductively activated by an external stimulus can be used. Also, tissue-specific promoters, such as pMADS3 promoter, may be used preferably.

In the present invention, the plant cells into which a vector is introduced are not particularly limited to particular forms as long as the cells can be regenerated into plants. They include, for example, cultured cell suspensions, protoplasts, leaf sections, and callus. A vector can be introduced into plant cells by known methods, such as the polyethylene glycol method, electroporation, *Agrobacterium* mediated transfer, and particle bombardment. Plants can be regenerated from transformed plant cells by known methods depending on the type of the plant cell. For example, petunia cells are cultured in the medium containing auxin (IAA: indole acetic acid) and cytokinin (BAP: benzylaminopurine)

to regenerate into shoots, which are subsequently grown on the medium containing IBA (indole butyric acid) for rooting and development (van der Meer, I. M. (1999). Methods Mol. Biol. 111, 327–334) Similar methods can be used to regenerate plants from torenia, tobacco and gerbera cells (Elomaa, P. et al. (1998). Plant J 16, 93–109).

According to the present invention, once a transformed plant is obtained, wherein the DNA of the present invention is integrated into the genome, it is possible to gain progenies from that plant body through sexual or vegetative propagation. Alternatively, plants can be mass-produced from breeding materials (for example, seeds, fruits, ears, tubers, tubercles, tubs, callus, protoplast, etc.) obtained from the plant, as well as progenies or clones thereof. The following are covered (but not limited) by the present invention: plant cells transformed with the DNA of the present invention; plant bodies including these cells; progenies and clones of the plant; and breeding materials obtained from the plant, its progenies and clones. The plants of the present invention are, without any particular limitation, flowering plants that undertake floral organogenesis, and ornamental plants. The latter are particularly preferred.

BEST MODE FOR IMPLEMENTING THE INVENTION

The present invention is illustrated in detail below with reference to the following examples but is not to be construed as being limited thereto.

EXAMPLE 1

Isolation of Genomic DNA Containing pMADS3

Figure 1:
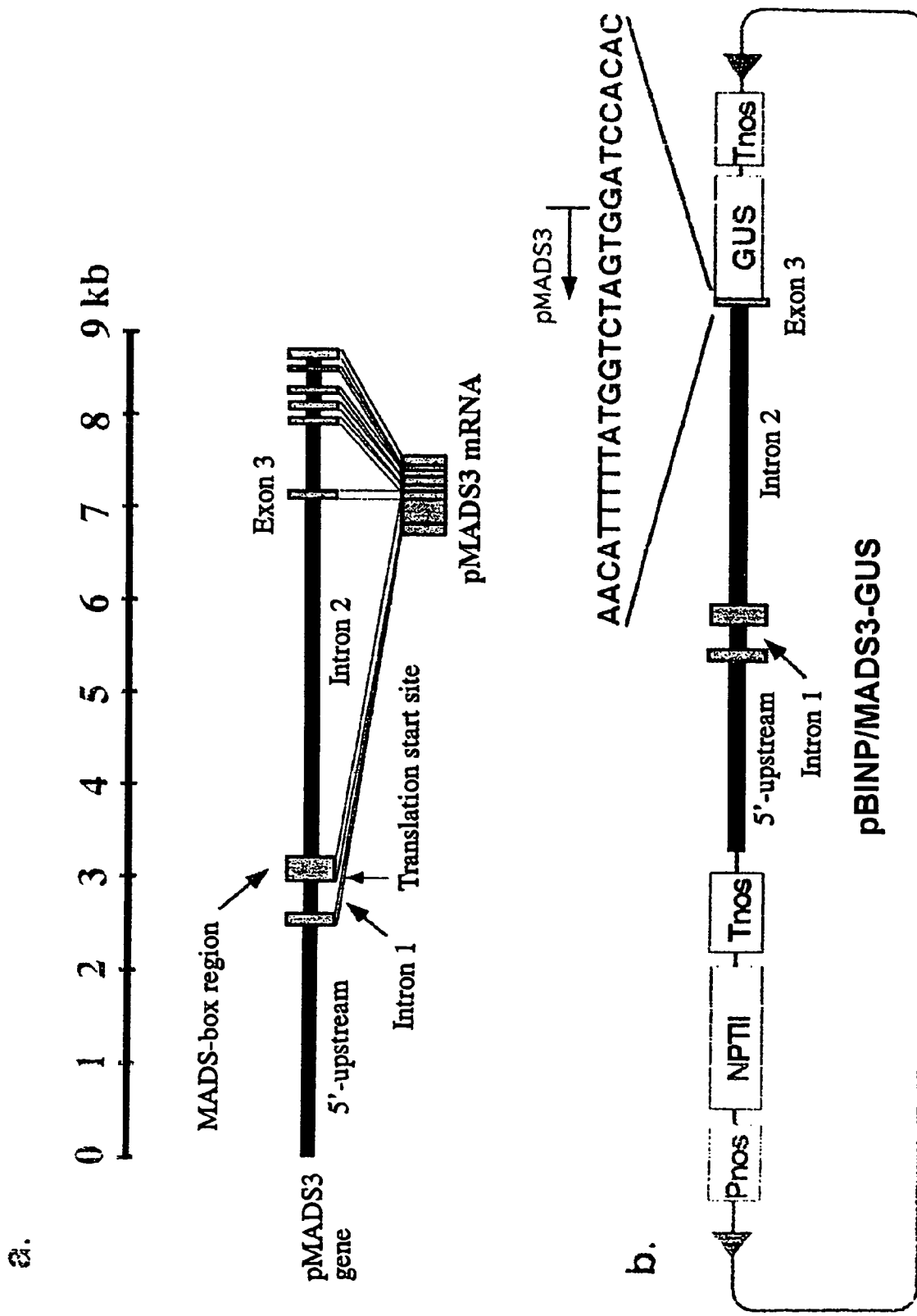
FIG. 1 depicts the structures of the pMADS3 and pMADS3-GUS genes. a, Genome structure of the pMADS3 gene. Boxes indicate exons. b, The construct for introducing the pMADS3-GUS gene. The sequence adjacent to the GUS gene and located in the vicinity of the 5' end of exon 3 is shown.

The pMADS3 cDNA was labeled with [$^{32}$P] dCTP by the conventional method using random primers to generate a radiolabeled DNA probe (Sambrook, J. et al. (1989). Molecular Cloning, 2 Edition (Cold Spring Harbor, Cold Spring Harbor Laboratory Press)). This probe was used for screening the petunia (*Petunia hybrida* var. Mitchell) genomic library that was constructed using EMBL3 vector (Stratagene). A genomic DNA fragment of approximately 8.9 kb in length contained in the resultant clone was subcloned into the SalI-SpeI site of pBluescript vector (Stratagene) (pBS/pMADS3). The nucleotide sequence of this fragment was determined (SEQ ID NO: 1), and the open reading frames were predicted based on the reported sequence of the cDNA (Tsuchimoto, S. et al. (1993). Plant Cell 5, 843–853) (FIG. 1a).

EXAMPLE 2

Construction of a Plant Expression Vector Containing a Polynucleotide Encoding pMADS3

To generate the pMADS3-GUS gene that induces silencing of the endogenous pMADS3 gene, the DNA fragment (approx. 7.2 kb) corresponding to the region extending from approximately 2.6 kb upstream of the putative transcription initiation site immediately downstream of the start site of intron 3 of MADS3 was ligated upstream of the coding region of GUS according to the following procedure. First, PCR was carried out using pBS/pMADS3 as a template, primer 1 (5'-GTGTGGATCCACTAGACCATAAAAAT-GTT-3'/SEQ ID NO: 2) and primer 2 (5'-AGTTGCAAGAT-GTACGTGGT-3'/SEQ ID NO: 3), initially for 45 seconds at 96° C., subsequently 30 cycles of 45 seconds at 96° C., 45 seconds at 55° C., and 4 minutes at 72° C., followed by incubation for 10 minutes at 72° C. (enzyme used was Pfu polymerase). The DNA fragment thus obtained corresponded to the region extending from an internal position of intron 2 to the 5'-terminal flanking sequence of exon 3. This fragment has a BamHI sequence in the vicinity of the 3'-end thereof. This DNA fragment was cleaved with NsiI and BamHI, and inserted into the NSiI/BamHI site of pBS/pMADS3 to restore a part of the pMADS3 gene. pBS/pMADS3-B was thus obtained. The pMADS3 sequence of about 7.2 kb in length was excised from pBS/pMADS3-B with SalI and BamHI after its nucleotide sequence was confirmed, and the excised fragment was inserted upstream (the SalI-BamHI site) of the coding region of β-D-glucuronidase (GUS) gene in plasmid pBINPLUS-GUS. This plasmid, pBINPLUS-GUS, was generated by inserting the XbaI-EcoRI fragment containing the GUS coding region and nopaline synthase (NOS) gene terminator, which fragment was excised from pBI221 (purchased from Clontech), between the XbaI and EcoRI sites of pBINPLUS (van Engelen, F. A. et al. (1995). Transgenic Res. 4, 288–290). As shown in FIG. 1b, the constructed pMADS3-GUS gene comprising the cauliflower mosaic virus (CaMV) 35S promoter region (P35S; 0.9 kb), a polynucleotide containing a part of the pMADS3 gene of the present invention (pMADS3; 7.2 kb) and the nopaline synthase gene terminator region (Tnos; 0.3 kb). In FIG. 1b, Pnos and NPTII denote the nopaline synthase promoter region and the neomycin phosphotransferase II gene, respectively.

EXAMPLE 3

Introduction of the Fusion Gene into *Petunia* Cells (1) *Agrobacterium tumefaciens* LBA4404 (purchased from Clontech) was cultured in L medium containing 250 µg/ml streptomycin and 50 µg/ml rifampicin at 28° C. Cell suspension was prepared according to the method described by Nagel et al. (Microbiol. Lett. (1990). 67, 325), and the plasmid vector constructed in Example 2 was introduced into the bacterial cells by electroporation.
(2) Introduction of the Polynucleotide Encoding each Fusion Gene into *Petunia* Cells
*Agrobacterium tumefaciens* LBA4404 obtained in (1) was cultured in YEB medium (see, DNA Cloning, Vol. 2, p. 78) with shaking (28° C., 200 rpm). The culture was diluted 20-fold with sterilized water, and cocultured with petunia (Surfinia) leaf disks. After 2 to 3-day culturing, the bacterium was eliminated in the medium containing antibiotics, and the medium was replaced every other week. Kanamycin resistance conferred by expression of the NPTII gene derived from PBINPLUS introduced with the aforementioned fusion gene was used to select transformed petunia cells. Calluses were induced from the selected cells, and then regenerated into plants according to a conventional method (Jorgensen, R. A. et al. (1996). Plant Mol. Biol. 31, 957–73).

EXAMPLE 4

Expression of the Endogenous pMADS3 Gene in a Transgenic *Petunia* Plant Transformed with the pMADS3-GUS Gene The expression of the endogenous pMADS3 gene in the petunia plant transformed with the pMADS3-GUS gene was examined by Northern blot hybridization. To generate the DIG-labeled RNA probe, the PstI-EcoRI fragment (nucleotide positions 517 to 1214) from pMADS3 cDNA (Tsuchimoto, S. et al. (1993). Plant Cell 5, 843–853) was subcloned into pBluescript vector, which was then cleaved with BglII (at the nucleotide position 572) and subjected to transcription reaction using T7 RNA polymerase in the presence of DIG-labeled UTP. Hybridization was performed according to the Boeringer's manual, except that the filter was washed for four hours at 68° C. after the reaction.

Figure 2:
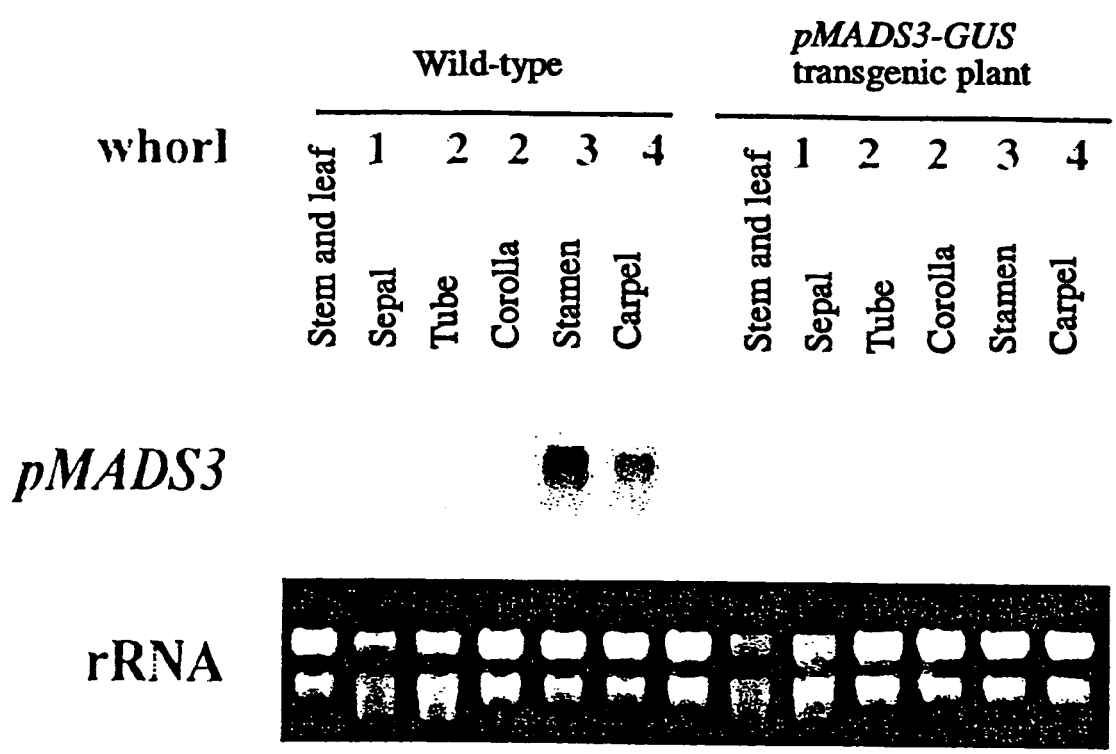
FIG. 2 is a photograph showing the silencing of the endogenous pMADS3 gene due to introduction of the pMADS3-GUS gene.

The expression of the endogenous pMADS3 gene is intrinsically localized in the stamens and carpels. However, hybridization using total RNA isolated from each floral organ of the pMADS3-GUS transgenic plant failed to detect the expression of the endogenous pMADS3 gene in the stamens and carpels in five of the twelve lines of the transgenic plants, revealing occurrence of silencing of the endogenous pMADS3 gene. FIG. 2 shows the result obtained from one of the five transgenic plant lines.

Molecular mechanisms for gene silencing are known to be categorized into two types, namely, post-transcriptional silencing and transcriptional silencing. Considering the fact that the DNA fragment from pMADS3 failed to exhibit any promoter activity in any of the transgenic plants tested (including those in which gene silencing did not occur), the gene silencing observed in this experiment is most likely transcriptional silencing (rather than post-transcriptional silencing) in which initiation of transcription is required.

EXAMPLE 5

Figure 3:
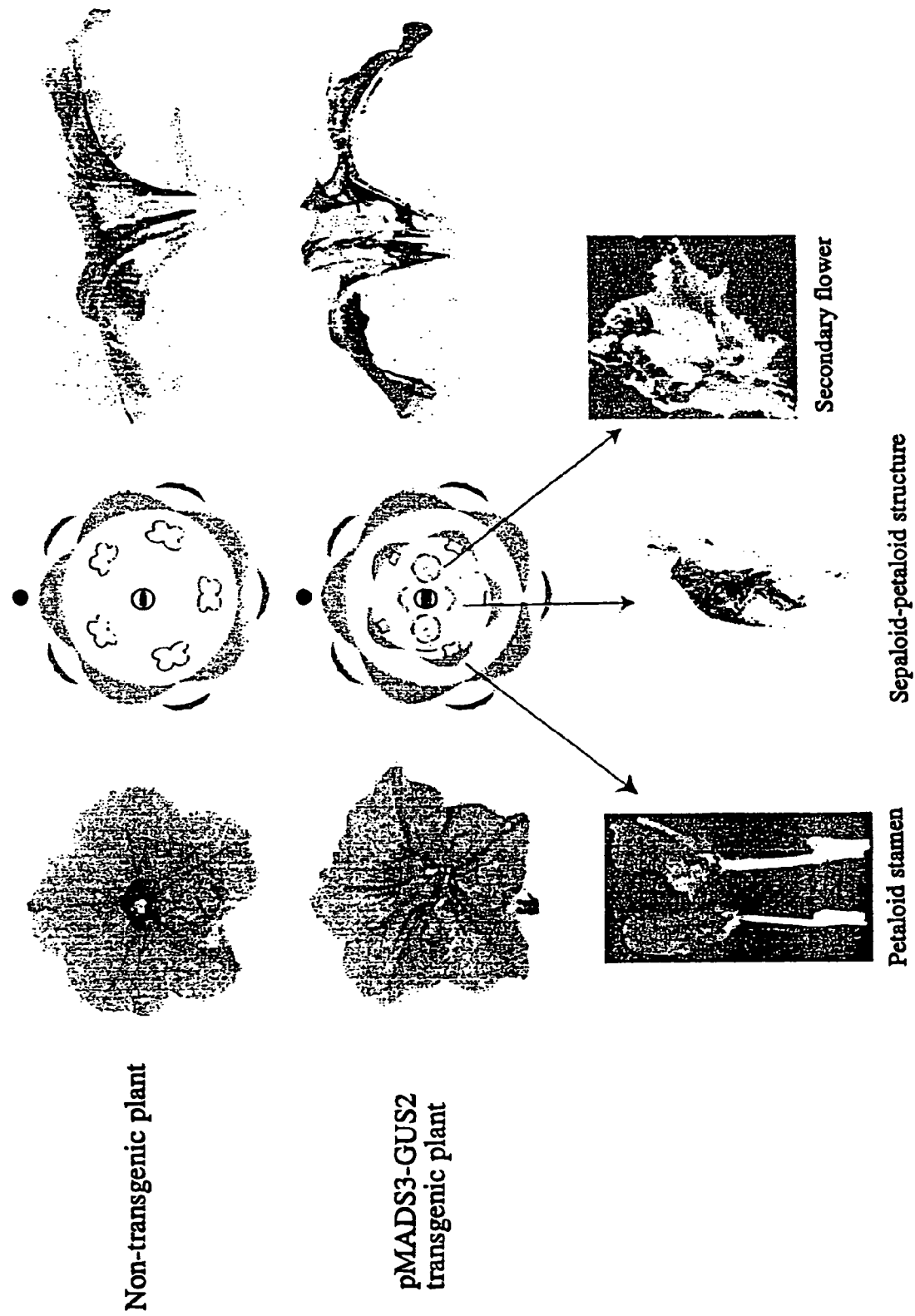
FIG. 3 is a photograph showing conversion of stamens into petals and formation of a secondary flower due to silencing of the pMADS3 gene.

Homeotic Transformation of Floral Organs in Transgenic *Petunia* Plants into which the pMADS3-GUS Gene has been Introduced All the transgenic lines in which the silencing of the endogenous pMADS3 gene occurred showed phenotypes as described below. As shown in FIG. 3, stamens were converted into petals in individuals from these lines. The degrees of the conversion varied depending on the lines: only anther tips were converted into small petals; almost no conversion was observed in the filaments in the lines showing weak phenotypes; whole stamens were converted into petals in the strains showing augmented phenotypes. The conversion of stamens into petals was not perfect even in the augmented phenotype lines, the anther structures remained and the pollens were formed. In contrast, the carpels appeared nearly normal. Single or multiple petaloid-sepaloid structures and buds of secondary flowers were formed in the concentric region between the whorls of stamens converted into petals and carpels. The number of such structures varied (1 to 4) among the lines and among the flowers produced on an individual plant. In the secondary flowers, the organs normally to be developed into stamens were converted into petals, showing that homeotic transformation occurred in the secondary flowers similar to primary flowers. Since secondary flowers usually stop growing at the stage of small buds, they are not observed from outside of the flowers.

The pMADS3 gene is structurally similar to the AGAMOUS gene, a member of Arabidopsis Class C genes, and is specifically expressed in the third and fourth whorl. Ectopic expression of this gene under the control of CaMV 35S promoter led to conversion of petals into stamens, suggesting that the pMADS3 gene is a petunia class C gene. However, it was reported that loss-of-function mutation of the AGAMOUS gene showed a phenotype in which petals occurred in the third whorl (region where stamens are developed) and, in addition, the whorls consisting of sepals and petals repeated inwardly (Yanofsky, M. F. et al. (1990). Nature 346, 35–39). The experiment conducted here has revealed that the loss-of-function phenotype of the pMADS3 gene is distinct from that of the AGAMOUS gene, suggesting that these class C genes have different functions.

INDUSTRIAL APPLICABILITY

The present invention provides a plant whose flower morphology has been altered by loss-of-function mutation of a MADS-box gene, and a method for producing said plant. The present invention enables generation of a great diversity of varieties in shorter periods of time than the conventional crossbreeding techniques. The present invention enables conferring multi-flower traits on plants, thereby producing ornamentally valuable garden plants. Molecules that can suppress the function of MADS3 gene may be used as an agent for this purpose.

---

The invention claimed is:

1. An isolated DNA molecule comprising the nucleotide sequence of SEQ ID No: 1.

2. A vector comprising the DNA molecule according to claim 1.

3. A transformed plant cell to which the DNA molecule according to claim 1 is introduced.

4. A transgenic plant comprising the transformed plant cell according to claim 3.

5. A progeny plant or clonal plant, each comprising a vector comprising the DNA molecule according to claim 1.

6. The plant according to claim 4, wherein said plant has an alteration in the flower morphology compared to the wild-type plant.

7. The plant according to claim 6, wherein said alteration in the flower morphology is at least one selected from the group consisting of conversion of stamens into petals, formation of secondary flowers and formation of sepaloid-petaloid structures.

8. A plant reproductive material comprising a vector comprising the DNA molecule according to claim 1.

9. A method for producing a plant having an alteration in the flower morphology, comprising the steps of:

(a) introducing the DNA molecule according to claim 1 or a vector carrying said DNA molecule into a plant cell;

(b) regenerating a plant from said plant cell; and (c) expressing said DNA molecule, thereby altering the flower morphology.

10. The method according to claim 9, wherein said alteration of flower morphology of plants is at least one selected from the group consisting of conversion of stamens into petals, formation of secondary flowers and formation of sepaloid-petaloid structures.

* * * * *

SEQUENCE LISTING

```
<160> NUMBER OF SEQ ID NOS: 3

<210> SEQ ID NO 1
<211> LENGTH: 8909
<212> TYPE: DNA
<213> ORGANISM: Petunia x hybrida
<220> FEATURE:
<223> OTHER INFORMATION: strain="Mitchell"
<220> FEATURE:
<223> OTHER INFORMATION: genomic DNA
<220> FEATURE:
<221> NAME/KEY: exon
<222> LOCATION: (2577)..(2728)
<220> FEATURE:
```

```
<221> NAME/KEY: intron
<222> LOCATION: (2729)..(2986)
<220> FEATURE:
<221> NAME/KEY: exon
<222> LOCATION: (2987)..(3224)
<220> FEATURE:
<221> NAME/KEY: intron
<222> LOCATION: (3225)..(7234)
<220> FEATURE:
<221> NAME/KEY: exon
<222> LOCATION: (7235)..(7316)
<220> FEATURE:
<221> NAME/KEY: intron
<222> LOCATION: (7317)..(8030)
<220> FEATURE:
<221> NAME/KEY: exon
<222> LOCATION: (8031)..(8092)
<220> FEATURE:
<221> NAME/KEY: intron
<222> LOCATION: (8093)..(8218)
<220> FEATURE:
<221> NAME/KEY: exon
<222> LOCATION: (8219)..(8318)
<220> FEATURE:
<221> NAME/KEY: intron
<222> LOCATION: (8319)..(8423)
<220> FEATURE:
<221> NAME/KEY: exon
<222> LOCATION: (8424)..(8469)
<220> FEATURE:
<221> NAME/KEY: intron
<222> LOCATION: (8470)..(8609)
<220> FEATURE:
<221> NAME/KEY: exon
<222> LOCATION: (8610)..(8651)
<220> FEATURE:
<221> NAME/KEY: intron
<222> LOCATION: (8652)..(8742)
<220> FEATURE:
<221> NAME/KEY: exon
<222> LOCATION: (8743)..(8909)
<220> FEATURE:
<221> NAME/KEY: MISC_FEATURE
<222> LOCATION: (5942)
<223> OTHER INFORMATION: Wherein n is G or A or T or C.
<220> FEATURE:
<221> NAME/KEY: MISC_FEATURE
<222> LOCATION: (6653)
<223> OTHER INFORMATION: Wherein n is G or A or T or C.
<220> FEATURE:
<221> NAME/KEY: MISC_FEATURE
<222> LOCATION: (6729)
<223> OTHER INFORMATION: Wherein n is G or A or T or C.
<220> FEATURE:
<221> NAME/KEY: MISC_FEATURE
<222> LOCATION: (6785)
<223> OTHER INFORMATION: Wherein n is G or A or T or C.
<220> FEATURE:
<221> NAME/KEY: MISC_FEATURE
<222> LOCATION: (6821)
<223> OTHER INFORMATION: Wherein n is G or A or T or C.
<220> FEATURE:
<221> NAME/KEY: MISC_FEATURE
<222> LOCATION: (6897)
<223> OTHER INFORMATION: Wherein n is G or A or T or C.
<220> FEATURE:
<221> NAME/KEY: MISC_FEATURE
<222> LOCATION: (6899)
<223> OTHER INFORMATION: Wherein n is G or A or T or C.
<220> FEATURE:
<221> NAME/KEY: MISC_FEATURE
<222> LOCATION: (6913)
<223> OTHER INFORMATION: Wherein n is G or A or T or C.
<220> FEATURE:
<221> NAME/KEY: MISC_FEATURE
<222> LOCATION: (7007)
<223> OTHER INFORMATION: Wherein n is G or A or T or C.
<220> FEATURE:
<221> NAME/KEY: MISC_FEATURE
```

```
<222> LOCATION: (7897)
<223> OTHER INFORMATION: Wherein n is G or A or T or C.
<220> FEATURE:
<221> NAME/KEY: MISC_FEATURE
<222> LOCATION: (7951)
<223> OTHER INFORMATION: Wherein n is G or A or T or C.
<220> FEATURE:
<221> NAME/KEY: MISC_FEATURE
<222> LOCATION: (7991)
<223> OTHER INFORMATION: Wherein n is G or A or T or C.
<220> FEATURE:
<221> NAME/KEY: MISC_FEATURE
<222> LOCATION: (8076)
<223> OTHER INFORMATION: Wherein n is G or A or T or C.

<400> SEQUENCE: 1
gtcgacctgc aggtcaacgg atcaatgatt ataaacgata tgcttctaga agaggacaca      60
aggaacctca agcttagaaa gcttataaaa aaaacttcac agattttgag aaaagcagat     120
gtcgctatat cttattgcca tagagaagca aatcatgtga ccaatttcat ggctaaattg     180
gcttcctcaa gttgaaatag tacactctat tattccttcc aacaactatc gaaataggtg     240
aagagactat ttcaactaga taagtgacaa ctttcaagca caagaagaag attcagcaaa     300
gctaacatat ttattactcc ctccgtccca aattgagtgt tttacttttc tttttgtttt     360
gtcccaaaat gagtgcgtca ttctatattt agtaagctga caattcaaac atcctacatg     420
gcagatttaa acccacaaat tcaaggaca ttttagtaca ttacacacat ctttcattta     480
gaaccacaca attgaaaagt ttccctatat ttttaaaatt ttgtgcccag tcaaactaag     540
acactcaatt tgggatggag ggagtagtta ataaaaatat tgtagatgtc gaaacgttct     600
ttcatagtaa agtctcttcc actatatgtt aaagtcatgc aagtttattt ttggaggtaa     660
ggtgcatgtc cccatcttct tcttgtgcaa ttgaatgagt gggcattgta ggagtcaagc     720
caaaaccccc ccaacaccta tagggaatat acctttggtg atggcttaat cttaattaga     780
aaaaaaattg agaagatcac tttcctgaat tctcaaaaat ctttgcaata ttcacgtagt     840
ctcaactttt tcaaaatgac acttagccca ttaagatttt gagaaatgga caagattgta     900
ttagtcccta tcataagaca cctcatgttt atatagcagc gaagcaaatt ttataaccta     960
ttaaattaat ggtgggcgaa atccgtttg caagcattaa agagttttta ttgaatgacg    1020
acccgcattc tggcttcctt tatttcaaag tggaagttgt acctagtgta cactggttag    1080
aagaagtgga catgacacat caaaaagtta cggcacacct ttgtaaataa cattcatttc    1140
taaccatatc ttctctgtga cttataccca tattgtagtt gcttctaggg ttccaccggt    1200
gtattcttaa ctaagcacaa aaaataaaat aaaatcttcc caggcccaag ttatgttagc    1260
cttagcagtt aatatgtgta ctccttaaag ggaatagaca ttttgaaata tacgcttcat    1320
agtcttttcc ccttatacgt gaatcttgtg acttcagtgg tcaagggaag ctaatgtatt    1380
ttcttgccaa acaatgttat gtcattgcaa tgttaaacat gtctcatggt tggcatagaa    1440
gaatgacaat tcctatgtga aaataagcat taataagagc aaaagaacaa gaatttaggc    1500
taatgtctag agaggactaa cttattgtaa cgtcgaatca gatcaaaagg gtaaggtcaa    1560
aggctaagta gtggcaaatt gagatgagag tgaaattgga tgaagaaatc atgataaccct   1620
aacaaagtag acaagaaaat gaaaaggtg gaaaagagga aattgaattt gttgtatatg    1680
tcattgagca taaccggcca tatagacaaa tttatgtcct tcttcccaaa gaaacaggta    1740
acttttggc atgatggtaa cttgatagat aagtggttgt tcatagatga gtttcaatag    1800
aaaagaaagt agagcactgg atgtcacatg gcagtcacct tctctgttgt cattgcaagt    1860
```

```
ttcactgatc tagttctttt ctctttcttt ttcccttgag tgatctattt atagtctgtg   1920
tttaatgtga gagataaaac aaaagatcac aaagtaaaaa ttatgtacac atagggttgg   1980
taaagttaac agaagaaaag tagtgatggt gggggggagaa taggatgtta aaagcaagga   2040
ttccaagtta gtttgggggg gggggggggg agggagtaa tgggatgtga agttcacatg    2100
tagaaataaa aaaattaaaa tatttgttgg aaaatattca aatggtccaa atcttaaagg   2160
gcttagaaga acattaaaag atctaatccc attttgaga agcatttaag cttgagtgta    2220
acctagtcca atgtttctct tcacccatca aacatcagag tcactttcag gggtcatttt   2280
ctcaactctg tccacttcct cccaccaccc acccactcc accccctct cttccaataa     2340 atgattacaa tctaacaaga aattagaata taaacaagag atcaagaaat atgaatggcc   2400
aagaaaggct gattatcatg agataattcc ctaattaacc atctatccta cttgttcaat   2460
acaagccaac aatctgaaaa agagaactat taaagaaata tgtcaaagtt taatgtaaat   2520
tagcataaga ataaacagac aaagaaaatt caagttagtt aatagtaaca taataaatta   2580
aaagaaacac tcttactttt ataaatacct atcccttagt gcaaactctc ttccattttc   2640
tgcatctatc ctctgcagat taatttgcaa aggaagaact aaaagcttct atctcttatt   2700
ccatctccaa atcttctttt cttatcaggt tagcaattaa actaaaaaca tttacacacc   2760
atgtcaaaaa aatcaatttg aaccattttt tgaatgtaac ataaaataag tggttggata   2820
ttgatcaatg caagatagtt tgagttagta tgattaggaa agtattcacc aaattcttta   2880
gcaatcatca ctgattgctt cattttagtt gtattgaaca ataaaaggtc attttttcca   2940
agtttgtcac atagtttttt tttttgtttt tttgtgtttg atataggtgc tgcaatggag   3000
ttccaaagtg atctaacaag agagatctct ccacaaagga aactaggaag aggaaagatt   3060
gagatcaaga ggatcgaaaa cacgacaaat cggcaagtca cttttgcaa gagacgcaat    3120 ggtttgctca aaaaagccta tgaattatct gtgctctgtg atgctgaagt tgctttgatt   3180
gtcttctcta gccgaggcag gctctatgag tatgccaaca acaggtaatc ttttaacaaa   3240
aaaaattaga aagtgttaat ttcagaaagt ttaatcttta ccttcttgag tctctacagc   3300
tttgtctagc tagctttacc tttcttcttc atttctcact cttcttttct tgcaattctg   3360
tttgtcttcc ttaaaagaga aaataatcgt gattggaaaa tttgcttgtg ttacagaatg   3420
cttaggaaga tctgaacttt aaaaggagaa agatcatgtt gttttgaagt ttttaaacta   3480 agagttttc cttctaacaa agaattgact ttcctttcct ttcttttttt attgtttaat    3540
aagttttgtt tgtttctatt tttgtgatcc caattttgtt aaaagacttg tagatgtata   3600
gatctgtttg ttgtaaaaat ttgggaaggt actcatcaca actctgagat cagcatagtt   3660
tcttcatttc agtttctgtt atgttttctc tctctcaaag atgaagcaag agagctgtcg   3720
agttctaatt cgcccattta gcccatcatt aaattagagt taatatggga tttagatctt   3780
atagtagtcc tttcacagcc aatgaaaatt cagattaggg ttttgtactt tgttaatagc   3840
tgtgcattac tgttttttgtc ttgaactttg tttctattgg cagagtcaaa cttgccctaa  3900
ttagggtttt ttttttcag ctagaaaatt attggtgttt ttccaattct ctaaattatt    3960
tcttctttaa caataaaatc tcagatatgc ttctcatgtg tagtgcaaat tctagtgttt   4020
tttcttgaaa taaaatgtag aaatccaatc agtgttcaaa gatcaattat agacaaaagt   4080
tgacattctt caaagtgttt ccgttttccc tttttcttta ctttcccttc ctatttctta   4140 aaatgttta caccgttgag gaaatggggt catctataca ctctactcta gcttagagtt    4200 ttaagaaacca gaaatttgtt ggggtgggtg gttggtgtaa gttttgtctc agttacaaga  4260
```

```
atctctggtc acgtcataca agattttaca cttgttgaca aatttgagaa aagacatatt    4320
gtgatgaggg aatggtttcc actgagctat ctcttaaatt tctatcttca attgtgtaaa    4380
attgaaaaca ctagctcctt attttctttt gagatatctc agtttaatgc tttcacaaag    4440
tttctgaaag tgttggaact taaacagcaa agaaacagaa gtggaagaaa gagaagtact    4500
aaaccaatga aaattttact cacttagcta agttttcaat aggatcttgt gcatagatat    4560
atttgcgtaa gacatgtaat agagttcggg ggggggggt ggatgggtgg gtgttgagaa     4620
agagatcaga catagatccg tacaatttat attccaacca atgagagagt tctgaactct    4680
ctggctttct atcttgcatg gtattggctg ctgaaaatgg acggttgtga tgtgatcaga    4740
tgagacagac aagactggat catactattc actttacctt acaacactgt aaaaatatta    4800
ctttattata gattattgat aaaatgcctt tgaaacaaaa ccctaggtgg gtaaaaacct    4860
agagttgaat ggtattaccc aaggaataac tggtacatga tgcgtggcat agatctgaac    4920
cgttgaaaca gtggaccaat catattgtgg gaacttgtgc cagcttggca gagagcagct    4980
aatcagtagc tcgacgaaat taaggttgta agtagactag gaaatgagag tcattcctca    5040
gtgttggttc ttttctttca atctgaaggt ctatactaga aaatattgta tcaatgtcat    5100
gtttgagtag acagattgag tctgactcaa agcaacactt tgttttttta tttaagctgt    5160
acgtgttggc ctaaattagc aagacataat aggtgtatta aatatggagt aagaaagtat    5220
ctggattttc attacctttt gaacaaaagg gtagtggtta aggcactctt tctatgtttg    5280
cttcaagtga acaagcactc gtgtctaaag atatatgaat agctgaaacc tctctcctta    5340
tgttttggtc cgtagtataa gctttgtttc acgctaaatt aatttctcac gaacttaggt    5400
acaacacttt ttgggggaaa atgacactct gtttttaaag tgtagttgta ataggaaacg    5460
agaaaatttt aagcttaaga gaagattaaa tttgaaactg atattgtcat gagcaatttg    5520
accagtgtgg gcaaataatt aatactctta tctattctat tttatgtagg gacgtttctt    5580
ttttgtgaat tttcaaaata aataaataac tttctaaatt aaaaaataat ttaaattaaa    5640
cttctatatt agtagcacaa atttgttgcc aatactaatc tcactttttt tattttggta    5700
atatttgtag taccccttc cccaatatat attcttttaa atgtttaaca tcacaagttt     5760
caaaaaaatt ttgattgata ggttcccaac actcttcact tctgctttta attcggtgct    5820
tatcaatact ttgtcaaata aattacgaca aggtaatta tacctgttgg ctgatttact     5880
atctttgtgt gaaaattagt gaagttcaat actagtaaat aaagatctgg gcaagcttgg    5940
tntacacata cttatcatca catcttatac agatccttt tcttgcctaa atattggaga     6000
gtacaattaa ttatctttct tcaatttccc atctttactt tgtcaagcca caaacgact     6060
gcaattttt tctcttgttt tcttgtattt tccccagtat ctcagcgaag ggtaaatctt     6120
tcatattgat ttatgcaaat gtgtcatttt ccttttcctt tttctccttt cttttcagcc    6180
tttacaccat taaggaagac ttagcaggtg ttaagaacac atagctaact acaactctac    6240
tgtgggaaat gtgttttcac aagttgcttg ttgacagcca aattgaaggg aaatgctctt    6300
tcttttgtta tgtagaatag ctaagcacta gaaacttata acctactagc aaatgatttt    6360
gtgcaagcaa atcttcttta acattattaa ttttcttcct taatctttta agtaccctga    6420
aagctctaga tttgctcgtc tttcatgttt cctaggggag ttgcaagatg tacgtggtca    6480
taagtaatag ccaaaaatca agaatacttt agcaaatgga acaaaccgtg gagatggctt    6540
tggaagatgt tcctttttgt gttcttaatt tttttttttt tttttttttg ggtggaggtg    6600
```

-continued

```
ggggtggtgg gggcttaaaa tggaacttaa attaatattt aaatatttac aanagtacag    6660
cggaaatagt taatgcatct atttcctctg tttaaaaaaa gatgaaccta ttttttttag    6720 ttcgttttana taaaatgatc tctttctaaa ttttgaaata aacttttact tttacccttta   6780 atganatgat atagcctaca aatatctatg acttacttta naccaagttt caaaagtcat    6840
ttcttcttta ttaaactccg cacaaagtta aatggattca tcattttga aacaaanana    6900 gtagtgccat ganacgctcc ttttcaaaaa catcagtaac aaaaggttgc ggacttgcgg    6960
tgtgcaaaca ctaattttgt tgtaaaaagg gtagttttcg tggtaanaaa atttgcctca    7020
ttttgctgac accataggag gtcacacaag agggaggcaa accttatttt ggaggaaggg    7080
tcaatagata gaatgctatt aggaaacttt taattcgatc ttgattttga taccgatcaa    7140
aaatatatta atctggttgt aacgcgatag ctgattatgg ttgtctataa attttaagat    7200
tgattagaaa ctgtctaaca ttttatggt ctagtgtgaa agcaacaatt gagaggtaca    7260
agaaagcttg ttcagattcc tcaaacactg gttcaattgc cgaagctaat gctcaggtat    7320
aatttcataa agtcctcttc ctacaacgaa gcctatatta tgacttgctt tgattattca    7380
aacttctttg agattatcga accatttctt atgttactta ttttgattcc ccttcccctt    7440
cagtaatgaa atgttttatt atattagact ttatagagat aaaatctact actacctcat    7500
ttcaaaaaaa aaaataacac atttccttat taaactttct attttaacac aagtattatg    7560
atatatataa aaccacaagt ttcaaaagtt tcatagtaac ataaatgtta tggaaccggg    7620
cttctattgt tattcactct acttaatcag ctgttctaaa gtcgtcaagg tggcacgatt    7680
ggattaagtt tttcatctag tattttattt tgaaagaatt agttttgttt tattttggtc    7740
gtttcttgaa agaaggcatt tgttttgttc tttctttctt ttggttctga actacttatg    7800
ttaaaccatg ttgatttggt ttagtaaaca accaagttaa actgaaatac atctaaggtc    7860
aaattctaag gtcattatag gagcatattc gtatctntag attcagttta catttagtta    7920
attaaaggcc ttctgtccat acataaagtt nttaaccaat atggattata agttgcaagc    7980
attatggatt nttgatctca ttaaatctta tgctgtttaa taaaacccag tattaccagc    8040
aagaagcctc caaactccgt gcacaaattg gaaatntgca gaaccagaac aggtgaaatt    8100
tattgttttc ttttttttt ctctttactt ttctattcac atttgttttc ttaccattt     8160 tttctcattt tgttatttgt tgttaatggt cctccttaac tcaactactt cgattcagga    8220
actttcttgg tgaatctctt gctgcactga atctcagaga tctgaggaac ctggaacaaa    8280
aaattgaaaa aggcattagc aaaatccgag ccaaaaggt gtacttacat tatttcccaa    8340
aatttcatat cacttttgtt tggtgaaatt ttcaactcct tgtgatggct atgatttact    8400
aacataccat tctcaaatta cagaatgagc tgttgtttgc tgaaattgag tatatgcaaa    8460
agagggtaag taatcgtgct tacataccat gaaagaatag tttcctaaag ttttaaacag    8520
atgttgaact tatgtgaaat tcataaagat caaaatgttc aagcctttta tgttcatgcc    8580
aaaaagtaac atatgttgat gcacagcagg aaattgattt acacaacaac aatcagtatt    8640
taagagcaaa ggtccatttc ttactcaaat atttgcttgt tagtccttaa atatattcct    8700
tcttctgcaa aaattattgg tttttgtatc taaattaaac agattgctga aactgagaga    8760
tcccagcaga tgaacttgat gcctgggagt tctagctatg accttgtgcc tcccagcag    8820 tcattcgatg cgcggaacta tctacaagtg aatggcttgc agaccaacaa ccattaccct    8880
agacaagacc aaccacctct tcaactagt                                      8909
```

```
-continued

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 2
gtgtggatcc actagaccat aaaaatgtt                                           29

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 3
agttgcaaga tgtacgtggt                                                     20
```